(12) United States Patent
Hayman et al.

(10) Patent No.: US 9,242,058 B2
(45) Date of Patent: Jan. 26, 2016

(54) TRACHEAL TUBE POSITIONING DEVICES AND METHODS

(75) Inventors: Sarah Hayman, Boulder, CO (US); Neville DeWitt Pierrat, Golden, CO (US); Roger Mecca, Corona Del Mar, CA (US); Olaf Lally, Galway (IE); Sean Morris, Co. Roscommon (IE); Hughie Keane, Leitrim (IE)

(73) Assignee: Covidien LP, Mansfield, MA (US)

( * ) Notice: Subject to any disclaimer, the term of this patent is extended or adjusted under 35 U.S.C. 154(b) by 1026 days.

(21) Appl. No.: 13/193,713

(22) Filed: Jul. 29, 2011

(65) Prior Publication Data

US 2013/0025602 A1    Jan. 31, 2013

(51) Int. Cl.
*A61M 16/04* (2006.01)
*A61M 25/10* (2013.01)
*A61B 1/06* (2006.01)
*A61B 1/267* (2006.01)

(52) U.S. Cl.
CPC ....... *A61M 16/0434* (2013.01); *A61M 16/0459* (2014.02); *A61B 1/0623* (2013.01); *A61B 1/267* (2013.01); *A61M 16/0463* (2013.01); *A61M 25/1002* (2013.01); *A61M 2205/32* (2013.01); *A61M 2205/6063* (2013.01)

(58) Field of Classification Search
CPC ............. A61M 16/0434; A61M 16/0463; A61M 16/0459; A61M 2205/6063; A61M 2205/32; A61M 16/04; A61M 16/0402; A61M 16/0418; A61M 16/0431; A61M 16/0445; A61M 25/10; A61M 25/1002; A61M 2025/1047; A61M 2025/1072; A61B 1/00082; A61B 1/06; A61B 1/0623; A61B 1/267; A61B 1/2673; A61B 1/2676; A61B 1/273; A61B 1/2733; A61B 1/2736
USPC ............. 128/200.26, 204.18, 206.29, 128/207.14–207.18; 604/100.01, 101.01, 604/102.01, 103.06, 103.07, 103.01; 600/109, 112, 114–117, 120, 194
See application file for complete search history.

(56) References Cited

U.S. PATENT DOCUMENTS

| | | | |
|---|---|---|---|
| 4,083,369 A * | 4/1978 | Sinnreich | 604/103.06 |
| 4,328,056 A | 5/1982 | Snooks | |
| 4,886,059 A | 12/1989 | Weber | |
| 4,913,642 A | 4/1990 | Weber | |
| 5,076,268 A | 12/1991 | Weber | |
| 5,308,323 A * | 5/1994 | Sogawa et al. | 604/95.03 |
| 7,963,911 B2 * | 6/2011 | Turliuc | 600/115 |
| 8,381,730 B2 | 2/2013 | Macan et al. | |
| 2003/0220542 A1 * | 11/2003 | Belson et al. | 600/109 |
| 2004/0220534 A1 | 11/2004 | Martens et al. | |
| 2008/0064930 A1 * | 3/2008 | Turliuc | 600/156 |
| 2008/0230070 A1 * | 9/2008 | Gregorian | 128/207.14 |
| 2010/0249639 A1 * | 9/2010 | Bhatt | 600/546 |

* cited by examiner

*Primary Examiner* — Annette Dixon
*Assistant Examiner* — Mark K Han
(74) *Attorney, Agent, or Firm* — Fletcher Yoder PC

(57) ABSTRACT

Various embodiments of tracheal tube assemblies disclosed herein may include a tubular body having an open distal end for ventilating a patient and a cuff disposed around the tubular body above the open distal end. The cuff may be adapted to be inflated to seal the cuff against a wall of a trachea of the patient. The cuff may include a first portion that spaces the tubular body a first distance from the tracheal wall when inflated and a second portion that spaces the tubular body a second distance from the tracheal wall when inflated. The second distance may be greater than the first distance.

8 Claims, 3 Drawing Sheets

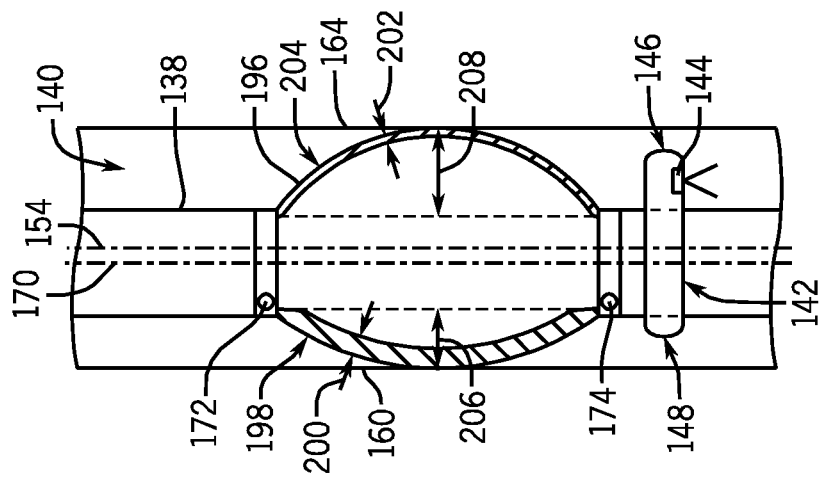
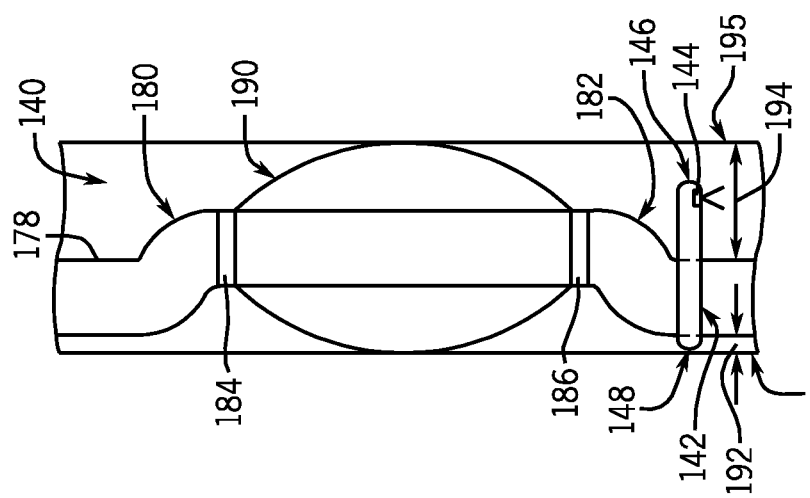
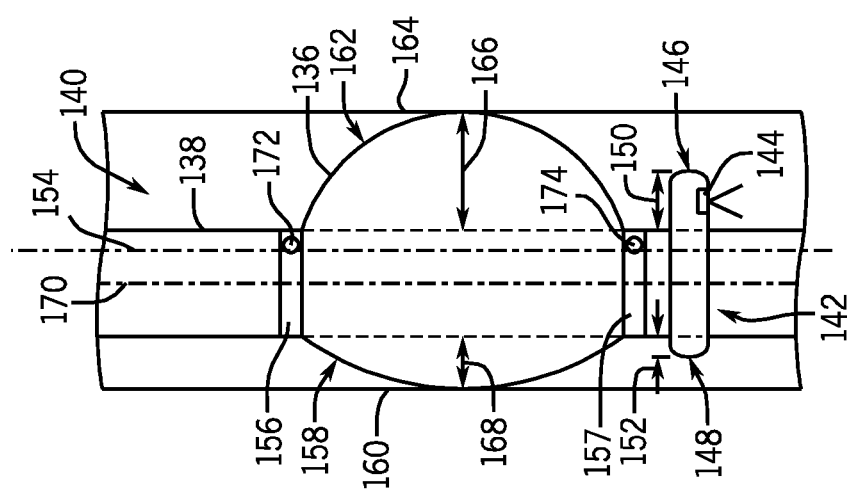

TRACHEAL TUBE POSITIONING DEVICES AND METHODS

BACKGROUND

The present disclosure relates generally to medical devices and, more particularly, to airway devices, such as tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air and medicaments into or out of a patient's airway. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient. For example, tracheal tubes may be used to control the flow of air or other gases through a patient's trachea. Such tracheal tubes may include endotracheal (ET) tubes, tracheostomy tubes, transtracheal tubes, and so forth.

To seal these types of tracheal tubes, an inflatable cuff may be provided. When inflated, the cuff generally expands into the surrounding anatomy, for example, into the trachea to seal the tracheal passage around the tube. Because the cuffs are generally made from a relatively thin and flexible material, the cuffs may inflate in such a way that the placement of the tubular body of the tracheal tube within the patient's airway is subject to substantial variations. For example, the cuffs may inflate to an irregular shape such that one side of the cuff has a greater incidence of wrinkles than another side of the cuff, and, accordingly, the tracheal tube may be positioned off center with respect to a central axis of the patient's trachea. In certain instances, such as when auxiliary devices (e.g., imaging devices) are coupled to the tracheal tube, it may be desirable to control the positioning of the tubular body of the tracheal tube within the patient's trachea. Accordingly, there remains a need in the art for improved tracheal tubes and cuffs that enable proper patient ventilation without the drawbacks associated with current designs.

BRIEF DESCRIPTION OF THE DRAWINGS

Advantages of the disclosed techniques may become apparent upon reading the following detailed description and upon reference to the drawings in which:

FIG. 6 illustrates a tracheal tube including a cuff having portions with different inflated resting radii and a collar mounted thereon;

FIG. 7 illustrates a tracheal tube including a curved tubular body, a cuff having portions with different inflated resting radii, and a collar mounted thereon; and FIG. 8 illustrates a tracheal tube including a cuff having portions with different wall thicknesses and a collar mounted thereon.

DETAILED DESCRIPTION OF SPECIFIC EMBODIMENTS

Figure 1:
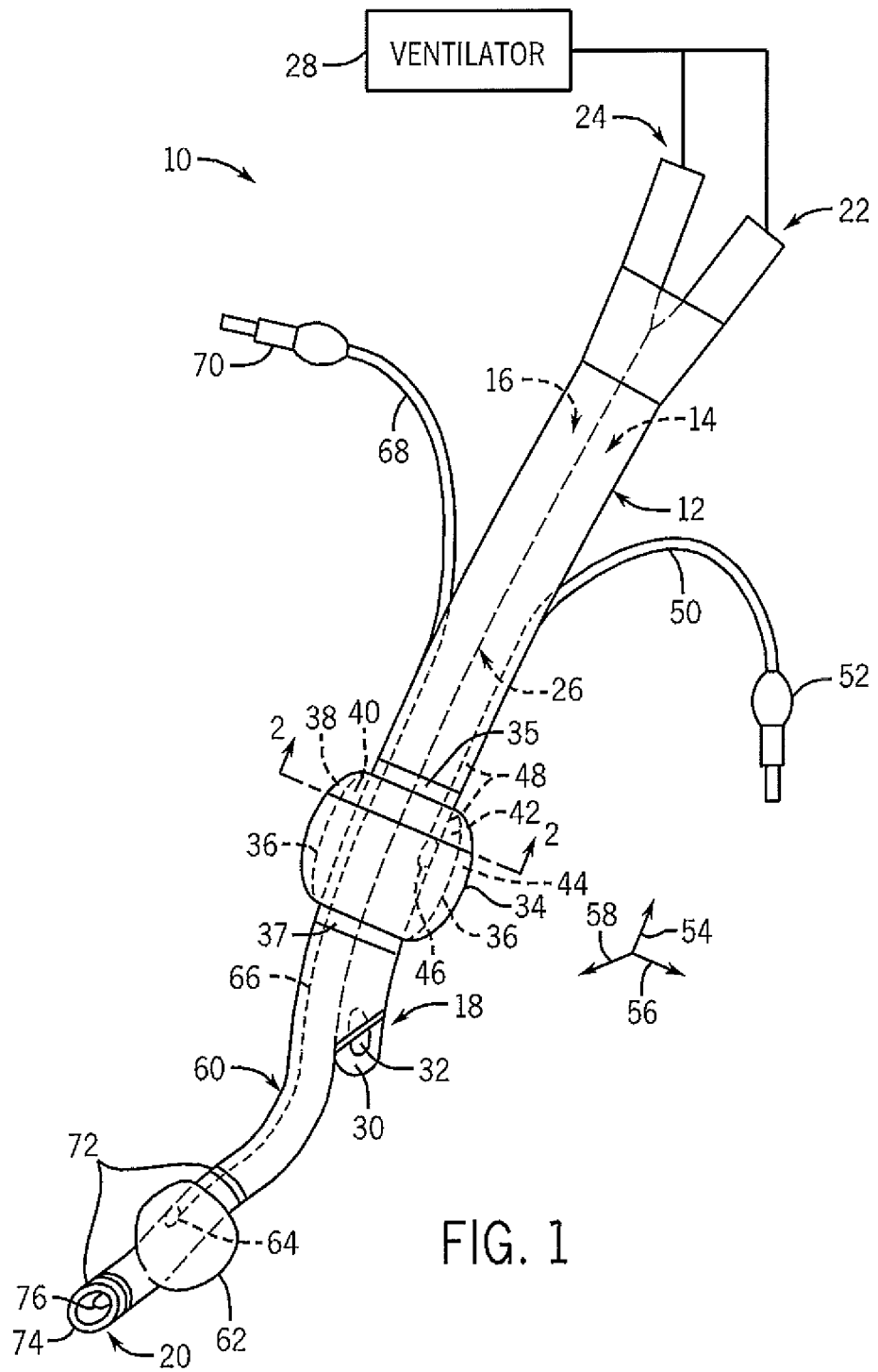
FIG. 1 is an elevational view of an endobronchial tube including a cuff adapted to enable control over the positioning of the endobronchial tube in a patient's trachea.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, provided herein are embodiments of medical cuffs capable of efficiently sealing the passage in which the cuff is inserted so that mechanical ventilation can be used to introduce air, oxygen, other gases, or medications into the lungs of a patient. The provided medical cuffs may have one or more features that enable an operator to inflate the cuff in a manner that enables control over the placement of a mounting structure relative to an axial axis of a patient's airway. For example, the medical cuffs provided herein may be used in conjunction with a variety of suitable medical devices including a tubular mounting structure on which the cuff is mounted during assembly or manufacturing. That is, the disclosed medical cuffs may be used in conjunction with an endotracheal tube, a tracheostomy tube, an endobronchial tube, a circuit, an airway accessory, a connector, an adapter, a filter, a humidifier, a nebulizer, a prosthetic, and so forth. When mounted on a tubular body, features of the provided cuffs may enable the operator to exhibit control over the position of the tubular body within the patient's airway.

For instance, in some embodiments, the cuff may include two or more separately inflatable regions adapted to be inflated and deflated as desired. In particular embodiments, the inflatable regions may have different inflation capacities, and, when fully inflated, the inflatable regions may position a tubular body of a tracheal tube off-center with respect to a central axis of the patient's trachea. The foregoing feature may be advantageous, for example, in instances in which a collared device is positioned below the cuff around the tubular body and protrudes farther outward from the tubular body one side than the other. In these instances, the side that protrudes farther outward may be aligned with the portion of the cuff that has a greater inflation capacity (e.g., volume) and, therefore, provides additional space within the airway to accommodate the collar protrusion. In other instances, however, the operator may desire the tubular body to be substantially in line with respect to the central axis of the patient's airway. In these embodiments, the inflatable regions may be inflated to approximately the same inflation capacity.

In some embodiments described below, the tracheal tube on which the medical cuff is mounted may be an endobronchial tube, although these embodiments are not meant to limit the cuffs to being mounted on this type of tracheal tube. Endobronchial tubes are double-lumen tracheal tubes that facilitate an airtight seal in the trachea and one stem of a patient's bronchus to allow independent ventilation of one lung. Generally, an endobronchial tube includes two tubes of unequal length that are attached to one another. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring gases to and from a patient.

While the total diameter of an endobronchial tube may be larger than that of a single lumen endotracheal tube, the diameter of each individual lumen of the endobronchial tube is relatively smaller than that of a single lumen endotracheal tube. Such a shift in diameter may be challenging for physicians during placement of an endobronchial tube. Because the endobronchial tube involves not only correct intubation within the trachea but also correct placement of the bronchial lumen within a left or right bronchial stem, physicians may use visualizing devices, such as bronchoscopes, to aid in the placement of the bronchial tube. However, commercial bronchoscopes are generally sized and shaped to be used in conjunction with the relatively larger lumen of a single-lumen endotracheal tube. As such, the bronchoscopes may not fit easily within either lumen of a double-lumen endobronchial tube.

The systems and devices provided herein offer an approach to overcoming these drawbacks by enabling clinicians to couple a visualization device to existing endobronchial tubes to facilitate better visualization of the endobronchial tube placement. For example, by enabling the clinician to inflate one portion of a disclosed cuff to a different volumetric capacity than another portion of the cuff, an imaging device may be accommodated in the patient's airway. That is, some embodiments may employ an imaging device, such as a camera mounted on a collar configured to be placed about a tubular body of the endobronchial tube, in conjunction with the disclosed cuffs to facilitate visualization of portions of a patient's airway. In particular embodiments, these features may be advantageous for use with dual-lumen endobronchial tubes during initial placement of the tubes in the patient's airway, when the patient is moved during a period of prolonged intubation, and periodically during a medical procedure.

The tracheal tubes, as provided herein, may be disposable rather than reusable, capable of conveying gas to and from the patient, capable of providing separate ventilation channels to the tracheal space and to an individual lung, and capable of enabling control over the positioning of the tracheal tube about a central axis of the airway. It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respiratory arrest. For further example, the tracheal tubes may be coupled to an adapter or connector that is configured to cooperate with control circuitry to activate valving that controls the airflow to and from the patient during inspiration and expiration.

Again, although the embodiments illustrated and described herein are discussed in the context of endotracheal tubes such as endobronchial tubes, it should be noted that presently contemplated embodiments may include the disclosed cuffs mounted on any portion of a variety of suitable airway devices. For example, the disclosed medical cuffs may be utilized in conjunction with a tracheostomy tube, a Broncho-Cath™ tube, a specialty tube, or any other airway device with a main ventilation lumen. Furthermore, as used herein, the term "tracheal tube" may include an endotracheal tube, a tracheostomy tube, a Broncho-Cath™ tube, a bronchoblocking tube, a specialty tube, or any other airway device.

Turning now to the drawings, FIG. 1 is an elevational view of an exemplary tracheal tube 10 configured to be placed in a patient's bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22 and 24 and distal ends 18 and 20. The tubular body 12 may include a divider 26 that divides the tracheal ventilation lumen 14 and bronchial ventilation lumen 16 and serves as a shared wall between them.

The tracheal lumen proximal end 22 and a bronchial lumen proximal end 24 may be outfitted with separate connectors that may be attached to a ventilation device 28 during operation. The ventilation device 28 may include a suitable controller (e.g., a processor-based control system) so that a clinician may direct airflow to and from both the tracheal ventilation lumen 14 and bronchial ventilation lumen 16. In other embodiments, either the tracheal ventilation lumen 14 or the bronchial ventilation lumen 16 may be blocked or otherwise closed such that only one of the two lumens of the tracheal tube 10 is operational. The tracheal lumen distal end 18 of ventilation lumen 14 terminates in an opening 30 and may be placed in a patient's trachea during operation to maintain airflow to and from the patient's lungs. A Murphy's eye 32 may optionally be present and may be located on the ventilation lumen 14 opposite the opening 30 to prevent airway occlusion when the tracheal tube assembly 10 is improperly placed within the patient's trachea.

As illustrated, a tracheal cuff 34 may encircle the tubular body 12 and be inflated to seal against the walls of a body cavity (e.g., a trachea). To that end, the cuff 34 has a proximal shoulder region 35 and a distal shoulder region 37 that facilitate attachment of the cuff 34 to the tubular body 12. Further, the illustrated cuff 34 is a segmented cuff including partitions 36 that divide the cuff 34 into a first segment 38, a second segment 40, a third segment 42, and a fourth segment 44. Each of the segments may be adapted to be separately inflated to a different volumetric capacity by the operator. For example, in the depicted embodiment, for illustration purposes, a single port 46 is shown coupling the cuff 34 to an inflation lumen 48 terminating in an inflation tube 50 connected to an inflation pilot balloon and valve assembly 52. However, in further embodiments, a separate inflation lumen may be provided for each segment or a valving arrangement may be provided to enable fewer inflation lumens to be employed. Nevertheless, the foregoing feature enables an operator to control the degree of inflation of the cuff at different radial locations around the circumference of the cuff 34.

By enabling the operator to control the inflation volumes present at different locations about the circumference of the cuff 34, the illustrated embodiment provides the operator a way to control the alignment of the tubular body 12 with respect to an axial axis 54 (e.g., of a patient's airway) at different positions along a radial axis 56 or a circumferential axis 58. For example, the operator may shift the location of the divider 26 along the radial axis 56 within a patient's airway to move the tubular body 12 closer to one side of the tracheal wall or another. For further example, in some embodiments, the operator may inflate or deflate the segments of the cuff 34 to position the divider 26 in a position that is substantially aligned with a central axial axis of the patient's airway, thereby centering the tracheal tube 10 in the patient's airway. Indeed, the segmented cuff 34 enables the operator to position the tubular body 12 within the patient's airway at any desired location along the radial and circumferential axes 56 and 58.

It should be noted that the tracheal ventilation lumen 14 may also include a suction lumen (not shown) that extends from a location on the tracheal tube 10 positioned outside the body when in use to a location on the tubular body 12 that terminates in a port located proximally to cuff 34 through which secretions may be aspirated. Further, bronchial ventilation lumen 16 is longer than tracheal ventilation lumen 14 and includes a distal portion 60 that extends past the tracheal lumen distal end 18. The bronchial ventilation lumen 16 may include a bronchial inflation cuff 62 that is configured to seal against the walls of a patient's bronchial stem. The cuff 62 may be inflated via a port 64 coupled to an inflation lumen 66 terminating in an inflation tube 68 connected to an inflation pilot balloon and valve assembly 70.

The tubular body 12 and the cuff 34 may be formed from materials having desirable mechanical properties (e.g., puncture resistance, pin hole resistance, tensile strength, and so forth) and desirable chemical properties (e.g., biocompatibility). Further, in one embodiment, the walls of the cuff 34 or the cuff 62 may be made of a polyurethane (e.g., Dow Pellethane® 2363-80A) having suitable mechanical and chemical properties. In other embodiments, the walls of the cuff 34 or the cuff 62 may be made of silicone or a suitable polyvinyl chloride (PVC). In certain embodiments, the cuff 34 or the cuff 62 may be generally sized and shaped as a high volume, low pressure cuff that may be designed to be inflated to pressures between approximately 15 cm $H_2O$ and 30 cm $H_2O$. Further, bronchial cuff 62 may be a different color or include other identifying markings that allow a user to differentiate between the tracheal cuff 34 and the bronchial cuff 62. Still further, the tracheal cuff 34 and/or the bronchial cuff 62 may be any suitable size or shape, including, but not limited to, tapered or ribbed cuffs.

In addition, in some embodiments, to assist in proper placement of the tube 10, one or more imaging devices may be placed at any appropriate location along the length of the tube 10. For example, an imaging assembly having a collar that is adapted to encircle the tubular body 12 in a location below the cuff 34 may be provided. The collar may include a portion that extends outward a greater distance from the tubular body on one side than on another to accommodate a camera that is provided for visualization of the patient's anatomy. For example, such visualization may be desirable as the double lumen tracheal tube 10 is inserted into the patient, when the patient has been moved into an alternate position, or at any other suitable time while the patient is intubated. In these embodiments, the segmented cuff 34 that enables the operator to adjust the position of the tubular body 12 within the patient's airway may be particularly advantageous. That is, it may be desirable to position the protruding camera below a segment of the cuff that is overinflated as compared to an opposite cuff segment that is underinflated since this arrangement may allow additional space to accommodate the camera.

During operation of the illustrated airway device, the tracheal tube 10 is inserted into the trachea of a patient and positioned within the left or right bronchial stem, and the tracheal cuff 34 and bronchial cuff 62 are inflated to the desired volumetric capacities to isolate the appropriate airway structures and position the tubular body 12 in the desired location. In embodiments in which an imaging assembly, such as a collared assembly including an imaging device, is coupled to the tubular body 12, the imaging device may guide tube placement. In other embodiments, to assist in proper placement of the tube 10, X-ray visible markings 72 may be placed at any appropriate location. For example, the markings 72 may outline a bronchial distal opening 74 or a side eye 76. In some embodiments, one or more of the disclosed visualization features (e.g., a collared imaging assembly, x-ray markings, and so forth) may be associated with the tracheal cuff 34 and/or the bronchial cuff 62. For instance, in some embodiments, it may be desirable to visualize the bronchial cuff 62, for example, during placement of the tracheal tube 10 in the patient's bronchial stem.

Figure 2:
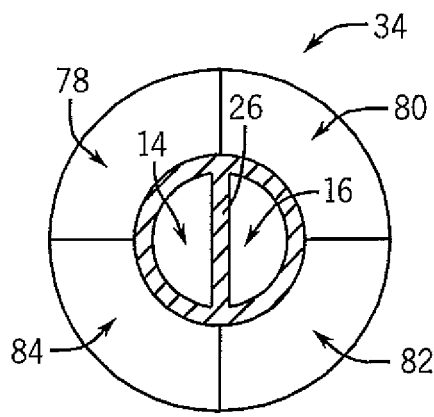
FIG. 2 is a cross-sectional view of the cuff shown in FIG. 1 illustrating segmentation of the cuff.

FIG. 2 is a cross-sectional view taken along line 2-2 of FIG. 1 illustrating features of the segmented cuff 34 in more detail. As shown, the illustrated cuff 34 includes a first inflatable region 78, a second inflatable region 80, a third inflatable region 82, and a fourth inflatable region 84. In accordance with a presently disclosed embodiment, each of the inflatable regions is adapted to be inflated and deflated independently. That is, the pressure of each inflatable region may be separately adjusted by an operator in order to position the tubular body 12 within the patient's airway in the desired location.

Figure 3:
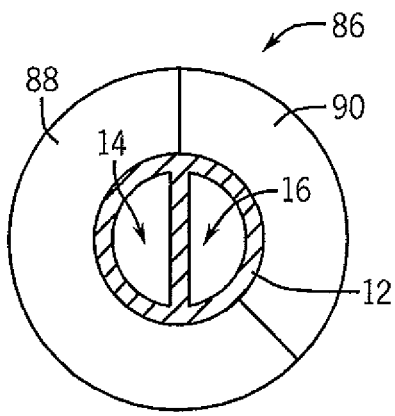
FIG. 3 is a cross-sectional view of a segmented cuff including a first inflatable region and a second inflatable region with different inflation capacities.

In the embodiment of FIG. 2, four inflatable regions 78, 80, 82, and 84 extending lengthwise along the length of the tubular body 12 are illustrated. However, in other embodiments, features of the two or more inflatable regions of the illustrated cuff 34 may be subject to considerable variations in quantity, size, shape, and placement based on the given application. As such, features such as the cuff 34 may have configurations other than those illustrated that are within the scope of the disclosed cuffs. For example, FIG. 3 illustrates a cross-sectional view of a cuff 86 including inflatable regions having substantially different inflation capacities. That is, the illustrated cuff 86 includes a first inflatable region 88 having a first inflation capacity and a second inflatable region 90 having a second inflation capacity that is less than the first inflation capacity. Although the illustrated view shows each of the regions 88 and 90 inflated to its full respective capacity, hem again, the volumes of the regions may be independently adjusted to position the tubular body 12 in the desired location within the patient's airway.

It should be noted that based on the intended use of the cuff, a different arrangement or quantity of inflatable regions may be provided. For example, in instances in which the cuff is coupled to an endotracheal tube, and the user desires the tubular body to be substantially centered within the patient's trachea, the cuff 34 of FIG. 2 may be chosen, and the inflatable regions may be filled to approximately the same volume with minor variations as necessary to achieve a substantially centered tubular body. However, in instances in which the cuff is coupled to an endobronchial tube including a collared camera assembly, the user may desire the tubular body to be off-center with respect to a central axis of the patient's trachea. In these embodiments, the cuff 86 of FIG. 3 may be utilized since the different inflation capacities of the inflatable regions may more easily provide the desired positioning.

Figure 4:
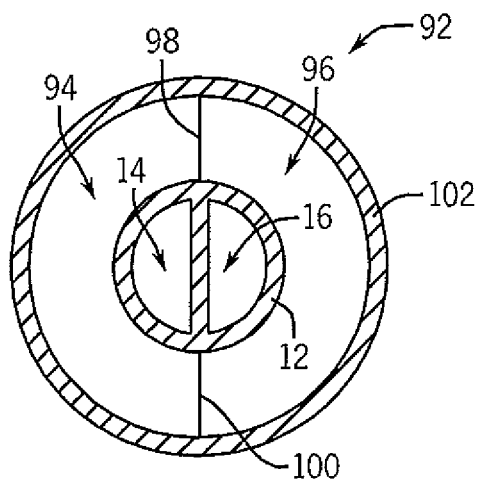
FIG. 4 is a cross-sectional view of a segmented cuff including an outer membrane disposed thereon.

Still further, in some embodiments, it may be desirable to reduce or eliminate the possibility of contact between the patient's airway and the interfaces disposed between the inflatable regions. To that end, one or more features may be provided that minimize such contact. For example, the embodiment of FIG. 4 illustrates a cuff 92 having a first inflatable region 94 and a second inflatable region 96 that are connected to one another at interfaces 98 and 100. A membrane 102 is disposed about the circumference of the cuff 92 to encircle the first inflatable region 94, the second inflatable region 96, and the interfaces 98 and 100. In certain instances, the foregoing feature may offer advantages over designs without a membrane. For example, in some embodiments, the membrane 102 may reduce the likelihood of grooves or creases forming in the cuff 92 in the areas around the interfaces 98 and 100 as the cuff is inflated to seal against a wall of a patient's airway.

Figure 5:
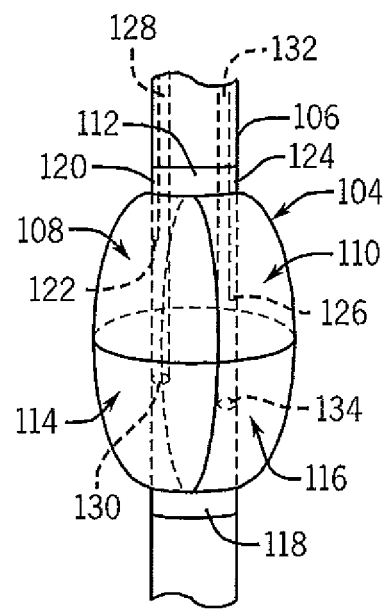
FIG. 5 is a perspective view of a tubular body having a cuff mounted thereon and segmented in a honeycomb arrangement.

As noted above, the cuffs of presently disclosed embodiments may take on various forms having a variety of arrangements of inflatable regions. For example, embodiments of the cuffs may have any combination of any quantity of vertically, horizontally, or angularly disposed inflatable regions. More specifically, in one embodiment illustrated in FIG. 5, a perspective view of a cuff 104 having a honeycomb structure and being mounted on a tubular body 106 is shown. In this embodiment, inflatable regions 108 and 110 are coupled to a proximal collar region 112 of the cuff 104, and inflatable regions 114 and 116 are coupled to a distal collar region 118 of the cuff 104. Here again, each inflatable region is configured to be inflated and deflated independently, for example, via separate inflation lumens. That is, in this embodiment, inflatable region 108 is inflated via inflation lumen 120 terminating in notch 122, inflatable region 110 is inflated via inflation lumen 124 terminating in notch 126, inflatable region 114 is inflated via inflation lumen 128 terminating in notch 130, and inflatable region 116 is inflated via inflation lumen 132 terminating in notch 134. However, in other embodiments, fewer lumens may be provided and one or more valving mechanisms may be employed to utilize the lumens to selectively inflate or deflate each of the inflatable regions.

FIGS. 6-8 illustrate further embodiments of the presently disclosed cuffs during operation in conjunction with imaging assemblies disposed about tubular bodies within a patient's airway. In particular, FIG. 6 illustrates an asymmetrical cuff 136 disposed about a tubular body 138 and inflated within a patient's trachea 140. A collar assembly 142 is also mounted on the tubular body 138 below the cuff 136. The collar assembly 142 includes an imaging device 144 disposed in a first portion 146 of the assembly opposite a second portion 148 of the assembly. As illustrated, the first portion 146 of the assembly protrudes outward from the tubular body 138 a first distance 150 that is greater than a second distance 152 that the second portion 148 of the assembly protrudes outward from the tubular body 138. The foregoing structure of the collar assembly 142 may accommodate the imaging device 144 and its associated electronics.

In some embodiments, the asymmetrical cuff 136 may include one or more features that enable the tubular body 138 to be positioned within the trachea 140 in a desired location with respect to a central axis 154 of the trachea 140. For example, the illustrated cuff 136 includes a proximal shoulder region 156 and a distal shoulder region 157 that couple to a first wall portion 158 that inflates to seal against a first side 160 of the tracheal wall. Similarly, a second wall portion 162 is disposed between the collar regions 156 and 157 and inflates to seal against a second side 164 of the tracheal wall.

When the cuff 136 is inflated, a resting radius 166 of the second wall portion 162 is greater than a resting radius 168 of the first wall portion 158. That is, the distance that the second wall portion 162 extends outward from the tubular body 138 is greater than the distance that the first wall portion 158 extends outward from the tubular body 138.

The foregoing feature enables the operator to adjust the position of a central axis 170 of the tubular body 138 with respect to the central axis 154 of the patient's trachea 140. For example, when fully inflated as shown in FIG. 6, the tubular body 138 is off-center with respect to the central axis 154 of the patient's trachea 140. This may be advantageous in embodiments in which the collar 142 is mounted on the tubular body 138 because the first portion 146 of the collar assembly 142 may be aligned underneath the second portion 162 of the cuff 136, where additional space is provided to accommodate the distance 150 that the collar assembly protrudes outward from the tubular body 138.

Further, it should be noted that in some embodiments, one or more indicators may be provided for the purpose of indicating to an operator which portion of the asymmetrical cuff is adapted to inflate to a larger resting radius and which portion is adapted to inflate to a smaller resting radius. For example, in the illustrated embodiment, indicators 172 and 174 are provided to indicate to a user that the portion 162 is capable of being inflated to a larger resting radius than portion 158. The indicators 172 and 174 may be of any quantity or type, including text, image, ink, chemical, or topographic markers. Indeed, the indicators 172 and 174 may take any form previously disclosed in U.S. Pat. No. 8,381,730, filed Jan. 29, 2009, which is hereby incorporated by reference. For instance, the indicators may be identified via touch, for example, in embodiments in which the indicators take the form of raised protrusions. Still further, the indicators 172 and 174 may be combined with any of the other presently disclosed embodiments to indicate to a user which portions of the adjustable cuffs correspond to which features (e.g., which segments correspond to which inflation capacities).

FIG. 7 illustrates a symmetrical cuff 190 having a proximal shoulder region 184 and a distal shoulder region 186 and being disposed about a tubular body 178 and inflated within the patient's trachea 140. It should be noted that in certain embodiments, the shoulder regions 184 and 186 may be inverted or non-inverted, depending on the given application. For example, in some embodiments, when the shoulder regions 184 and 186 are inverted, the length of the portion of the tubular body 178 that is disposed between the shoulder regions 184 and 186 may be shorter than the length of the portion of the tubular body 178 that is disposed between the shoulder regions 184 and 186 when the shoulder regions 184 and 186 are not inverted.

In the illustrated embodiment, the collar assembly 142 is also mounted on the tubular body 178 below the cuff 190. As before, the collar assembly 142 includes the imaging device 144 disposed in the first portion 146 of the assembly that protrudes outward from the tubular body 178 a greater distance than the second portion 148 of the assembly. In this embodiment, however, the tubular body 178 includes a first curved portion 180 and a second curved portion 182 that accommodate the protruding first portion 146 of the collar assembly 142.

In this embodiment, when the cuff 190 is inflated, the portion of the tubular body 178 that is distal to the curved portion 182 is offset with respect to the portion of the tubular body 178 that is disposed between curved portion 180 and the curved portion 182. Accordingly, a distance 192 from the tubular body 178 to a first portion 193 of the tracheal wall is greater than a distance 194 from tubular body 178 to a second portion 195 of the tracheal wall. As such, in this embodiment, the protruding portion 146 of the collar assembly 142 is accommodated by providing curved portions 180 and 182 in the tubular body 178.

Still further, FIG. 8 illustrates another embodiment of a cuff 196 disposed about the tubular body 138 and inflated within the patient's trachea 140. The collar assembly 142 is also mounted on the tubular body 138 below the cuff 196. As before, the first portion 146 of the collar assembly 142 protrudes outward from the tubular body 138 a greater distance than the second portion 148 of the assembly. However, in this embodiment, the wall thickness of the cuff 196 is variable about its circumference to facilitate offsetting of the central axis 170 of the tubular body 138 with respect to the central axis 154 of the patient's trachea when the cuff 196 is inflated.

The illustrated cuff 196 includes a first wall portion 198 having a first thickness 200 that is greater than a second thickness 202 of a second wall portion 204. Accordingly, when the cuff 196 is inflated as shown, a resting radius 206 of the wall portion 198 is less than a resting radius 208 of wall portion 204. The foregoing feature of the cuff 196 may allow for accommodation of the protruding portion 146 of the collar assembly 142 below the portion 204 of the cuff 196 with the larger resting radius 208.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube assembly, comprising:
  a tubular body having an open distal end for ventilating a patient;
  a cuff disposed around the tubular body above the open distal end and configured to be inflated to seal the cuff against a patient's tracheal wall, wherein the cuff comprises a first inflatable chamber and a second inflatable chamber separated from the first inflatable chamber by a partition, wherein the first inflatable chamber comprises a first arc greater than 180 degrees of a cuff circumference and the second inflatable chamber comprises a second arc less than 180 degrees of the cuff circumference such that a cross-sectional geometry of the cuff is asymmetrical; and
  an annular collar mounted to and disposed about the tubular body between the cuff and the open distal end, wherein the annular collar comprises an imaging device disposed in a first portion of the annular collar opposite a second portion of the annular collar.

2. The tracheal tube assembly of claim 1, wherein the first portion of the annular collar extends outward from the tubular body a first amount, the second portion of the annular collar extends outward from the tubular body a second amount less than the first amount, and the first portion of the annular collar is aligned with the first inflatable chamber of the cuff.

3. The tracheal tube assembly of claim 1, comprising a first indicator disposed on a portion of the tubular body or a portion of the cuff, wherein the position or form of the first indicator is configured to indicate the position of the first inflatable chamber or the second inflatable chamber with respect to the tubular body.

4. The tracheal tube assembly of claim 1, wherein the first inflatable chamber and the second inflatable chamber are configured to be separately inflated.

5. The tracheal tube assembly of claim 1, comprising a first inflation lumen extending from a proximal portion of the tubular body to the first inflatable chamber of the cuff and a second inflation lumen extending from the proximal portion of the tubular body to the second inflatable chamber of the cuff, wherein the first inflation lumen is configured to enable airflow to the first inflatable chamber of the cuff, and the second inflation lumen is configured to enable airflow to the second inflatable chamber of the cuff.

6. The tracheal tube assembly of claim 1, wherein the cuff is configured to adjust a position of the tubular body with respect to an axial axis of the tracheal wall.

7. The tracheal tube assembly of claim 6, wherein the tubular body is off center with respect to the axial axis of the tracheal wall when the cuff is inflated.

8. The tracheal tube assembly of claim 3, wherein the first indicator comprises a marking or a protrusion.

* * * * *